US008505781B2

(12) United States Patent
Crawford et al.

(10) Patent No.: US 8,505,781 B2
(45) Date of Patent: Aug. 13, 2013

(54) FRAGRANCE DISPENSING PUMP HEAD

(75) Inventors: John C. Crawford, Mahopac, NY (US); Kiat-Cheong Toh, Forest Hills, NY (US); Douglas Mooney, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 296 days.

(21) Appl. No.: 12/747,998

(22) PCT Filed: Dec. 13, 2007

(86) PCT No.: PCT/US2007/087351
§ 371 (c)(1),
(2), (4) Date: Jun. 14, 2010

(87) PCT Pub. No.: WO2009/075687
PCT Pub. Date: Jun. 18, 2009

(65) Prior Publication Data
US 2010/0264169 A1    Oct. 21, 2010

(51) Int. Cl.
*B67D 1/07*    (2006.01)
*B65D 88/54*    (2006.01)
*B65D 83/00*    (2006.01)
*B05B 15/00*    (2006.01)
*A24F 25/00*    (2006.01)

(52) U.S. Cl.
USPC .................. 222/192; 222/402.17; 222/321.7; 239/289; 239/57

(58) Field of Classification Search
USPC .......... 222/192, 402.17, 321.9, 321.7, 321.1, 222/401; 239/34, 304, 305, 289, 333, 60, 239/53, 54, 55, 56, 57
See application file for complete search history.

(56) References Cited

U.S. PATENT DOCUMENTS

| | | |
|---|---|---|
| 611,008 A | 9/1898 | Gerstendorfer |
| 849,211 A | 4/1907 | Daly |
| 2,131,975 A | 10/1938 | Elsie |
| D177,420 S | 4/1956 | Lipman |
| 2,779,624 A | 1/1957 | Friedman |

(Continued)

FOREIGN PATENT DOCUMENTS

GB    2 435 874    9/2007

OTHER PUBLICATIONS

International Search Report from the International Searching Authority [EP] for corresponding International Application No. PCT/US2007/087351 dated Sep. 3, 2008.

*Primary Examiner* — Kevin P Shaver
*Assistant Examiner* — Stephanie E Williams
(74) *Attorney, Agent, or Firm* — Judy W. Chung

(57) ABSTRACT

A dispensing pump including a pump mechanism and a pump bead is provided. The dispensing pump head includes an upper portion and a lower portion. The lower portion has a structure for attaching the dispensing pump to the container. The upper portion and the lower portion each has: (1) an internal area combining to form an enclosed space for containing a second product, and (2) a respective peripheral wall. The pump mechanism also includes a dispensing channel for the first product that extends between the upper and the lower portion. There is an aperture in either peripheral walls or a space between the respective peripheral walls. Upon the actuation of the dispensing pump, the upper portion passes into the lower portion to force air from the enclosed space and the second product is emitted through one of the apertures in either peripheral walls or the space therebetween.

13 Claims, 9 Drawing Sheets

(56) References Cited

U.S. PATENT DOCUMENTS

| | | |
|---|---|---|
| 3,330,481 A | 7/1967 | Dearling |
| D210,516 S | 3/1968 | Mascia |
| 3,558,055 A | 1/1971 | Storchheim |
| D238,322 S | 1/1976 | Kulhanijian |
| 3,940,024 A | 2/1976 | Russo et al. |
| 3,955,706 A | 5/1976 | Whitaker |
| 4,084,732 A | 4/1978 | Dearling |
| 4,200,229 A | 4/1980 | Spector |
| 4,243,159 A | 1/1981 | Spatz |
| 4,263,734 A | 4/1981 | Bradshaaw |
| 4,341,348 A | 7/1982 | Dearling |
| 4,346,059 A | 8/1982 | Spector |
| 4,372,490 A | 2/1983 | Le Caire, Jr. et al. |
| 4,544,592 A | 10/1985 | Spector |
| 4,549,693 A | 10/1985 | Barlics |
| 4,747,539 A | 5/1988 | Spector |
| D296,526 S | 7/1988 | von Schuckmann |
| 4,759,501 A * | 7/1988 | Silvenis et al. ............. 239/6 |
| 4,858,758 A | 8/1989 | Mitchell et al. |
| 5,029,700 A | 7/1991 | Chen |
| 5,156,283 A | 10/1992 | Sampson |
| 5,163,616 A | 11/1992 | Bernarducci et al. |
| 5,165,603 A | 11/1992 | Hahn |
| D351,794 S | 10/1994 | Foster |
| 5,351,851 A | 10/1994 | Powell |
| 5,360,145 A * | 11/1994 | Gueret ...................... 222/190 |
| 5,364,027 A | 11/1994 | Kuhn |
| 5,379,917 A | 1/1995 | Brown et al. |
| D355,845 S | 2/1995 | Wass |
| D356,249 S | 3/1995 | Abfier et al. |
| 5,595,324 A | 1/1997 | Brown et al. |
| D385,792 S | 11/1997 | Sayers et al. |
| D388,706 S | 1/1998 | Mascitelli |
| D389,407 S | 1/1998 | Mascitelli |
| D396,188 S | 7/1998 | Sayers |
| 5,776,561 A | 7/1998 | Lindauer |
| 5,799,826 A | 9/1998 | Brown et al. |
| D399,745 S | 10/1998 | Mascitelli |
| D399,746 S | 10/1998 | Hayataka |
| 5,871,126 A | 2/1999 | Bennett et al. |
| D414,697 S | 10/1999 | Sayers |
| D419,878 S | 2/2000 | Kerr et al. |
| 6,062,425 A | 5/2000 | Brown et al. |
| D436,039 S | 1/2001 | Moretti |
| D442,854 S | 5/2001 | Weber |
| 6,394,264 B2 | 5/2002 | Riviello, Jr. |
| 6,533,144 B2 | 3/2003 | Davies et al. |
| D489,616 S | 5/2004 | Bakic |
| 6,729,506 B2 | 5/2004 | Brown et al. |
| 6,769,631 B2 | 8/2004 | Brown |
| 7,981,367 B2 * | 7/2011 | Kvietok et al. ............. 422/123 |
| 2002/0030116 A1 * | 3/2002 | Brown ........................ 239/59 |
| 2002/0108968 A1 | 8/2002 | Dumont |
| 2009/0001190 A1 * | 1/2009 | Liou et al. .................. 239/34 |

* cited by examiner

FRAGRANCE DISPENSING PUMP HEAD

CROSS-REFERENCE TO RELATED PATENT APPLICATIONS

This application is a National Stage entry under 35 U.S.C. §371 of International Application No. PCT/US2007/087351, filed Dec. 13, 2007, the entirety of which is incorporated herein by reference.

This invention relates to a pump head for a dispensing pump where the pump head contains a fragrance. More particularly the invention relates to the structure for a fragrance dispensing pump head.

BACKGROUND OF THE INVENTION

There are many devices for delivering a fragrance to a room or other space. Many of these are designed solely to deliver a fragrance. These range from potpourri, scented candles and units that utilize an electrical source. There also are fragrance units that are a part of another article. These other articles can be bottles and other containers such as are set out in U.S. Pat. Nos. 5,165,603 and 6,769,631. Each of these patents discloses having a fragrance dispensing unit attached to the upper or the lower part of a container. U.S. Pat. No. 4,341,348 discloses an aerosol container with a fragrance dispensing unit attached to the top part of the aerosol container. U.S. Pat. No. 3,955,706 discloses a fragrance unit that can be adhesively attached to the inside of a waste container. A fragrance unit can also be a part of the closure for a container. Such closures are disclosed in U.S. Pat. Nos. 2,131,975; 4,858,758 and 6,394,264. However, there is no disclosure of a structure whereby the fragrance is incorporated into a dispensing pump unit, such as a palm top pump unit. Containers that utilize palm top pumps are used mainly in the bathroom and in the kitchen. These are two areas where fragrances are useful in maintaining a fresh scent environment. Further since the fragrance unit would be a part of the dispenser pump that is in motion during use, there is an induced flow of air through the dispensing pump head during each dispensing which aids in the flow of the fragrance into the room.

Except for units that are disclosed in U.S. Pat. No. 6,769,631, the prior art units where the fragrance is a part of the container are of the passive type. The fragrance is dispensed into a room solely by the convection of the air in the room. In U.S. Pat. No. 6,769,631 there is disclosed a base unit which is actuated during a dispensing to assist in the flow of the fragrance from the base unit. However, this requires a costly unit to be added to the container. The dispensing unit of this application has a dynamic flow of air through the fragrance unit when a part of the contents of the container are dispensed, but requires no additional physical structure to the container or to the pump for the dynamic flow. The pump actuator functions to dispense product from the container and in addition as the holder and the dynamic dispenser for a fragrance. Optionally the dispenser pump also can have a passive fragrance delivery section. This present dispensing pump is a cost effective way to deliver a fragrance to a kitchen or a bathroom.

BRIEF SUMMARY OF THE INVENTION

The present invention is directed to a dispensing pump that functions to dispense a first product from a container and which also emits a volatile substance such as a fragrance as a second product. In addition, the invention is directed to such a dispensing pump in combination with a container. The dispensing pump is comprised of a pump head, a pump mechanism, a dip tube and a closure which attaches the dispensing pump to the container. The pump head is on one end of the pump mechanism and the dip tube on the other end of the pump mechanism. The container closure usually is associated with the pump head and attaches and seals the assembly of the pump head, dip tube and pump mechanism to the container.

The pump head is comprised of an upper portion and a lower portion. The upper portion has an actuator top surface to be contacted by a person's hand to actuate the pump mechanism and dispense a first product from the container. The lower portion usually includes the pump mechanism and the container closure. Either the upper portion or the lower portion, or both, have an internal area for containing the second product, which preferably is a fragrance. There is a first product dispensing channel extending through the internal area of the pump head to the pump mechanism and dip tube at one end and to an exit to the exterior at a second end. This dispensing channel flows the first product from the container through the pump mechanism and pump head to the exterior. The pump mechanism receives the first product from the container through the dip tube. The upper portion internal area has a top wall actuator surface, and an upper portion peripheral sidewall depending downwardly from the top wall. The lower portion internal area has a lower portion bottom wall and a lower portion peripheral sidewall extending upwardly from the bottom wall. The upper portion internal area and the lower portion internal area combine to form an enclosed space. The upper portion peripheral sidewall and the lower portion peripheral sidewall can overlap, but with a space between the peripheral sidewalls. Upon depressing the upper portion actuator surface the first product is dispensed from the container and the second product from the upper portion internal area and/or the lower portion internal area through the space between the peripheral sidewalls, and optionally through apertures that may be provided in the peripheral sidewalls. After an initial use, and when not dispensing the first product, some second product will flow to the exterior through the space between the upper portion peripheral sidewall and the lower portion peripheral sidewall and through any optional peripheral sidewall apertures that may be provided. The lower portion also may have one or more auxiliary areas for containing additional second product. These auxiliary areas can have apertures through which the second product is released to the exterior and/or it can be released to the lower portion internal area and from the lower portion internal area.

In the embodiment where either, or both, the upper portion peripheral sidewall and the lower peripheral sidewall have one or more apertures the dispensing of the second product will be accelerated when the first product is being dispensed from the container by the flow of the second product also through the apertures. After a dispensing of the first product there will be a flow of the second product through the space between the sidewalls and through the apertures for a passive delivery of the second product.

The pump head upper portion internal area and lower portion internal area will be of a size and shape to accommodate the second product, which preferably is a fragrance. These internal areas preferably will be cylindrical, in a generally circular, oval or multi-sided shape. The auxiliary areas will be areas available in the structure of the lower portion. The second product preferably will be a solid or a semi-solid fragrance or a fragrance adsorbed or absorbed onto or into a solid material which can be an organic or an inorganic material. It also can comprise bead-like particles. The second product can be located above and/or below the dispenser spout channel that delivers the first product to the exterior for use.

DETAILED DESCRIPTION OF THE INVENTION

The invention will be described in its preferred embodiments with reference to the drawings. These preferred embodiments can be modified but such modifications remain within the concept of the present invention.

Figure 1:
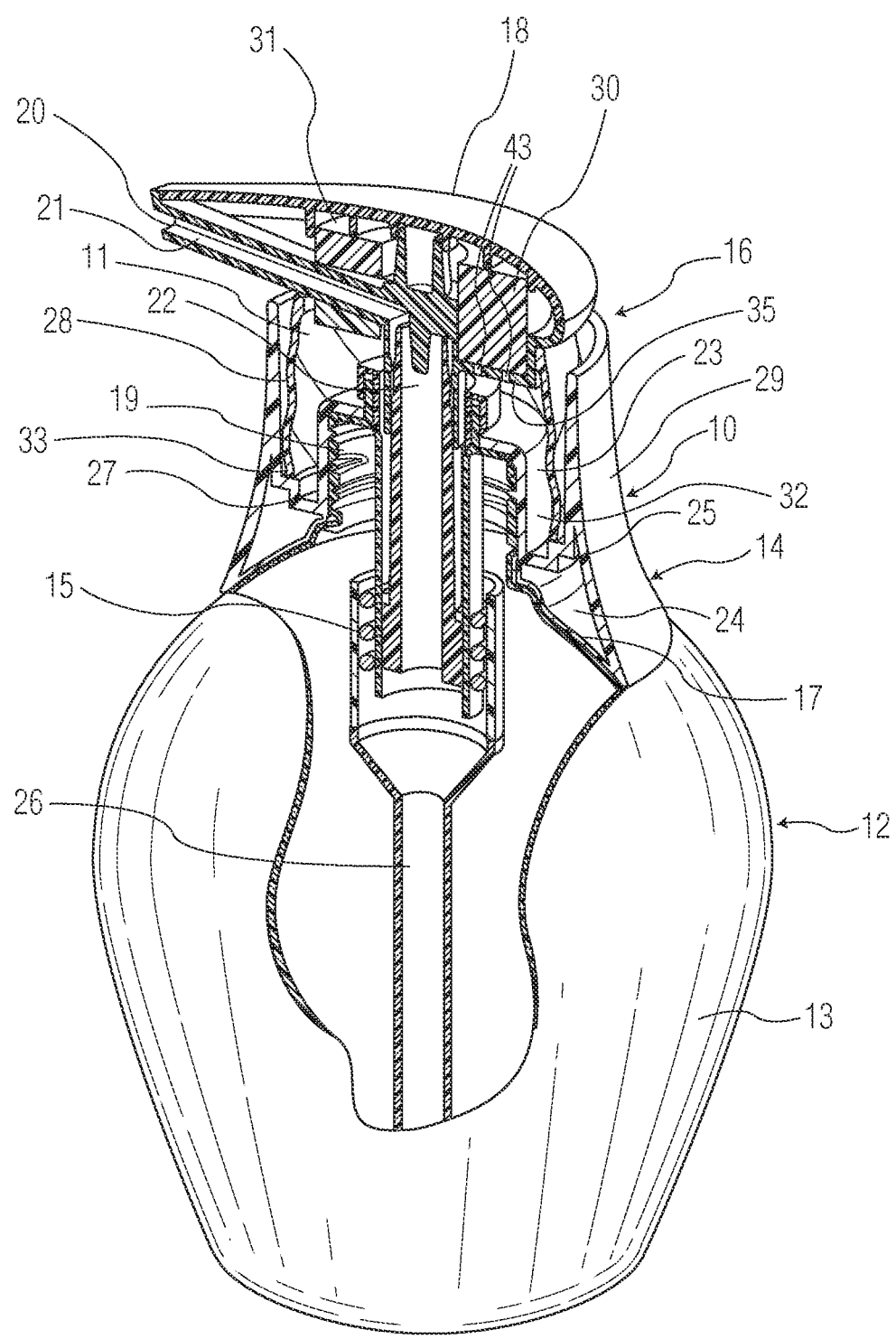
FIG. 1 is an elevation view partially in section of the container and dispensing pump with a fragrance second product in an upper portion internal area of the pump head.
Figure 2:
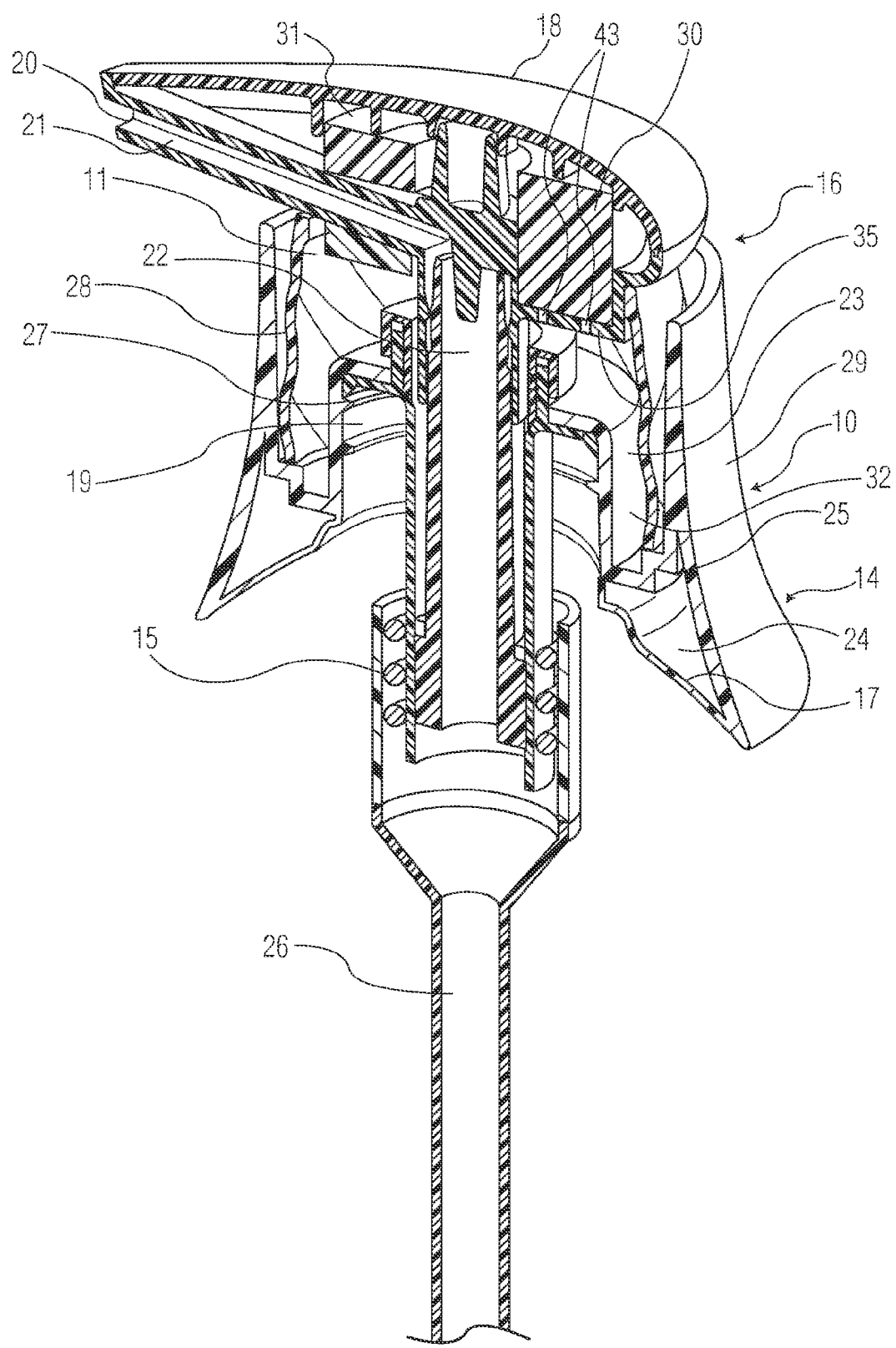
FIG. 2 is a perspective view of the dispensing pump of FIG. 1 in cross-section.

FIG. 1 is a perspective view in partial cross-section showing the container 12 and the dispensing pump 10. FIG. 2 is a cross-sectional view of the dispensing pump 10 alone without container 12. The dispensing pump 10 is shown in each view in a closed position. This is the position in which the container 12 and the dispensing pump 10 are shipped and sold. It also is the fully actuated position during use when the dispensing pump 10 is completing a dispensing stroke. The container 12 has a container sidewall 13. The dispensing pump 10 is comprised of a pump head having a lower portion 14 and upper portion 16. The upper portion top actuating surface 18 has a depending upper portion peripheral sidewall 28. Contained in the upper portion is a spout 20, spout channel 21 and a second product 30 contained within region 31 of upper internal area 11. Second product support wall 35 supports part of the second product 30. This support wall 35 will be discontinuous and can be spoke-like to support the second product 30 but not to separate it from the remainder of upper internal area 11, and/or have apertures 43. The second product optionally is a fragrance unit and is shown as a solid substance. However, it can be in other forms. When a fragrance unit, the fragrance will permeate into upper internal area 11 from which it can be dispensed. The upper portion 16 is integrally connected to the lower portion 14 which in turn is attached to the neck of container 12. The lower portion 14 has a lower portion bottom wall 25 and an upwardly extending lower portion peripheral sidewall 29 from the bottom wall. Lower portion inner wall 23 also extends upwardly from the lower portion bottom wall 25. The lower portion inner wall 23 is in a circular cross-section to form a cylindrical shape with threads 19 on an inner surface. It can be of other shapes. The threads 19 mate with the threads 27 on the neck of container 12 to attach the pump dispensing pump 10 to the container 12 Passing through the lower portion 14 is first product channel 22 which is connected to pump mechanism 15, which in turn is connected to dip tube 26 which extends into container 12. The pump mechanism is comprised of an accumulator chamber, a piston that traverses the accumulator chamber, an inlet valve and an outlet valve. The inlet valve is adjacent to a dip tube that delivers a liquid through this valve to the accumulator chamber. The outlet valve is at the other end of the accumulator chamber and adjacent to the first product channel 22. The first product channel 22 passes through lower portion internal area 32 and upper portion internal area 11, and at an upper end connects to spout channel 21 which terminates in spout 20. Also a part of lower portion 14 is auxiliary area 24 formed by lower portion peripheral sidewall 29, auxiliary area lower wall 35 and lower portion bottom wall 25. The lower portion internal area 32 and/or the auxiliary area 24 also can contain second product. When both contain second product, and the second product is a fragrance, more fragrance can be delivered to a room. This can be in a higher concentration for a shorter period of time or in a lower concentration over a longer period of time.

In the dispensing pump 10 position that is shown in FIG. 1 the lower edge 33 of upper portion peripheral sidewall 28 is in a close to contacting state with the lower portion bottom wall 25. This arrangement of the upper portion peripheral sidewall 28 and the lower portion bottom wall 25 creates a seal for the second product 30 in the upper portion internal area 11 prior to sale. When the second product 30 is a fragrance, some of the fragrance will escape the dispensing pump 10 around the upper portion peripheral sidewall edge 33 and pass between the lower portion peripheral sidewall 29 and the upper portion peripheral sidewall 28 to the exterior. However, this will not be a significant amount. Further, prior to the first use of the dispensing pump the pump head can be sealed with a shrink-wrap or other seal around its periphery to prevent fragrance loss prior to purchase.

Figure 3:
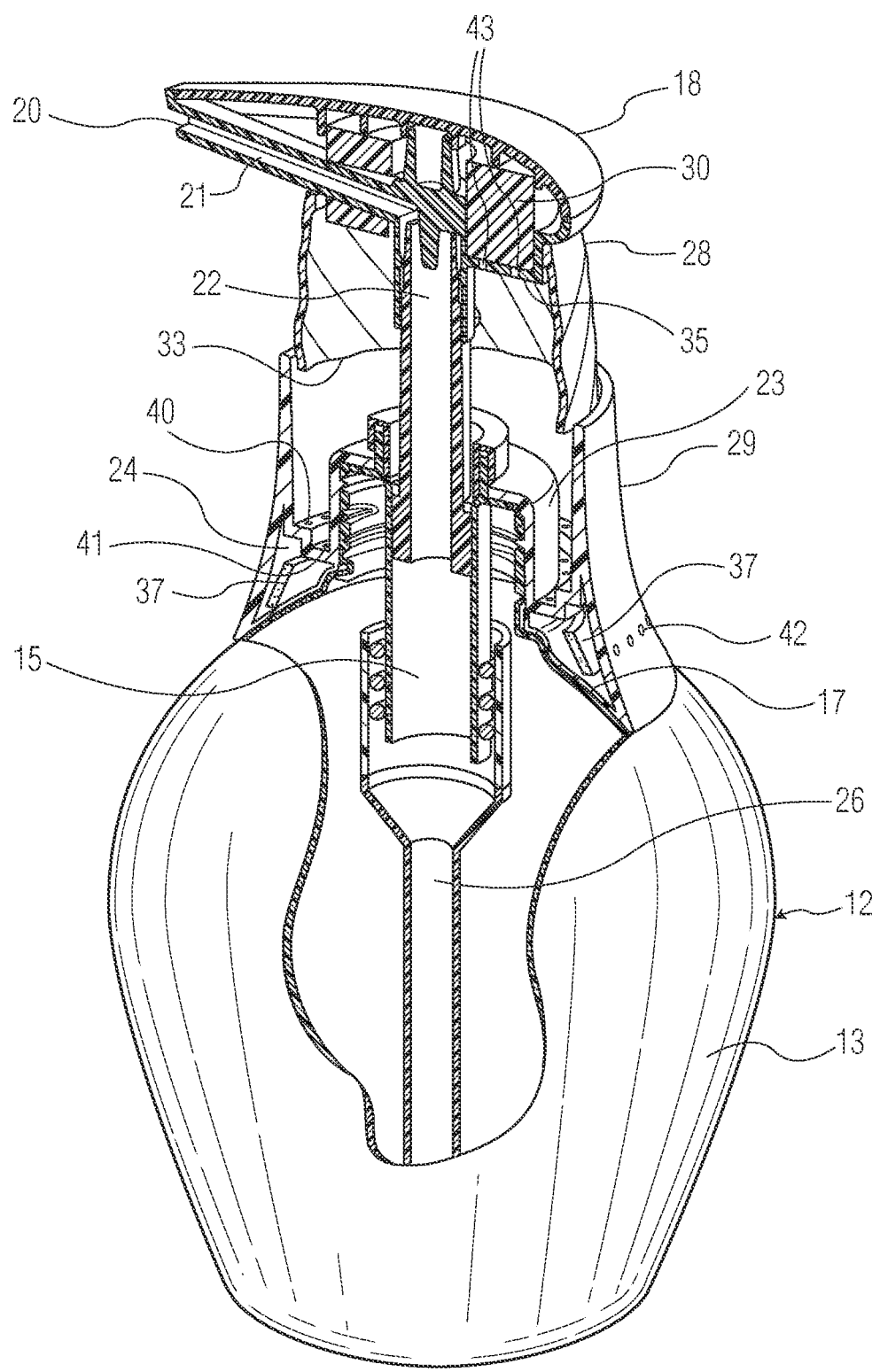
FIG. 3 is a perspective view partially in section of the container of FIG. 1 with a fragrance second product in the upper portion internal area and also in the lower portion auxiliary area of the pump head
Figure 3A:
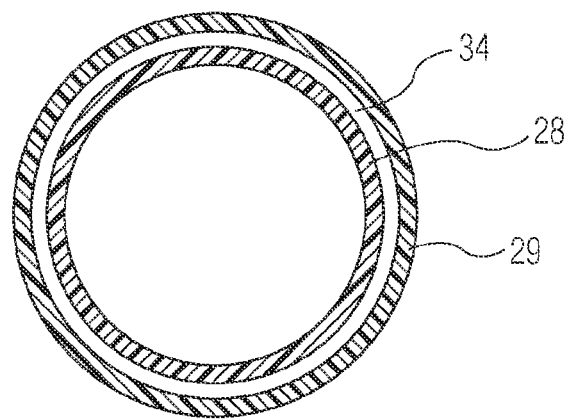
FIG. 3A is a top plan view of the space between the upper peripheral wall and the lower peripheral wall.
Figure 3B:
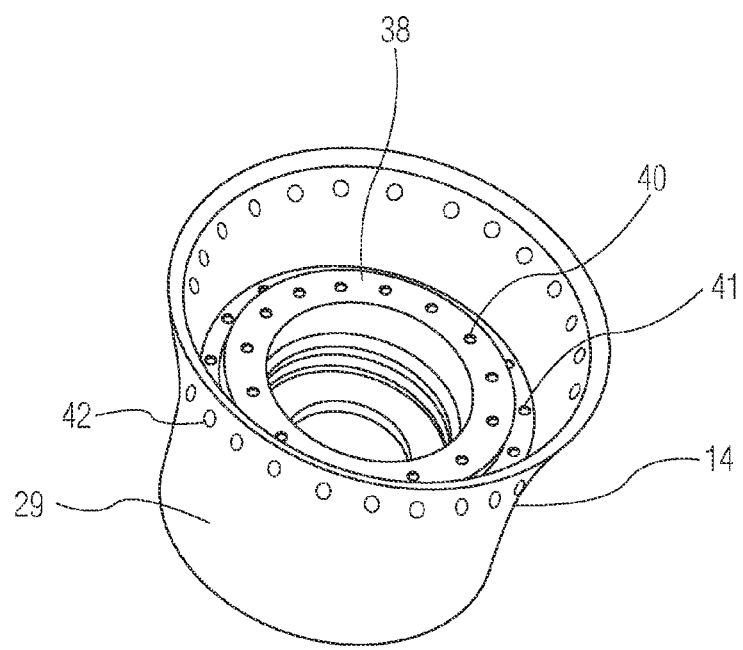
FIG. 3B is a perspective view of the lower portion along with the structure to attach the lower portion to the container.

The dispensing pump 10 in an open condition and ready for dispensing is shown in FIG. 3. The parts of the container and the pump head remain the same as in FIGS. 1 and 2 and will not be described again. Suffice it to say that the pump head is adjusted for use in the usual way by a rotation of the upper portion 16. This unlocks dispensing pump 10 with the upper portion 16 extending upward. In order to dispense some of the first product from the container 12 the top actuation surface 18 is depressed which causes the upper portion 16 to pass into lower portion 14 and for the pump mechanism 15 to be actuated to thereby dispense the first product from container 12 through first product channel 22 and spout channel 21. Concurrently, some of the second product 30 is forced through gap 34 between upper portion peripheral sidewall 28 and lower portion peripheral side wall 29. This portion of the second product is forced out through gap 34 by the air from the upper portion internal area 11 and the lower portion internal area 32 being forced out through the gap 34. This gap 34 between the lower portion peripheral sidewall 29 and the upper portion peripheral wall 28 is shown in more detail in FIG. 3A. In this embodiment the lower portion 14 will also contain some second product. This is shown a second product 37 in the form of a strip in auxiliary area 24. This auxiliary area 24 is created by lower portion peripheral wall 29, lower portion auxiliary area wall 17 and lower portion bottom wall 25. There are optionally a series of apertures 42 in lower peripheral sidewall 29 to vent the space 24. There also are a series of apertures 40 and 41 in lower portion bottom wall 25 as more specifically shown in FIG. 3B. These apertures 40/41 vent a second strip product 37 from lower portion auxiliary area 24 to the lower portion internal area 32. When the second product in auxiliary area 24 is a fragrance these apertures 40/41 and 42 will vent the fragrance respectfully to the lower portion internal area 32 and to the exterior.

Figure 4:
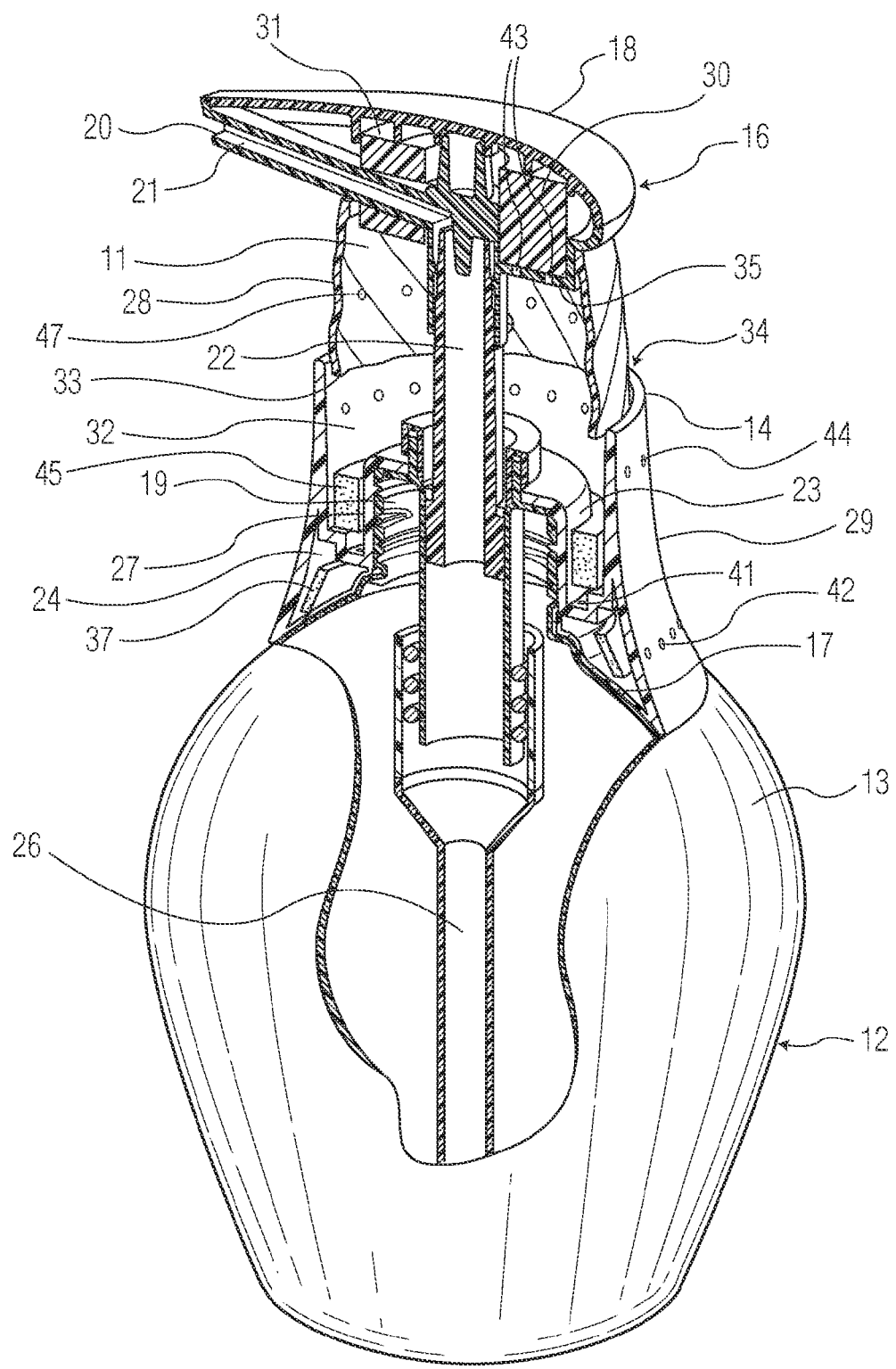
FIG. 4 is a perspective view partially in section of the pump head shown in FIG. 1 with solid and bead fragrance units in the lower portion and a fragrance solid unit in the upper portion along with apertures in the lower portion.

FIG. 4 is an embodiment of the container 12 and the dispensing pump 10 of FIG. 3 whereby there is an amount of second product 37 in lower portion auxiliary area 24 and an additional amount 45 of second product 30 is formed around lower portion inner wall 23 in the lower portion internal area 32. Upon the actuation of the dispensing pump 10 of FIG. 4 the second product 30/45/37, which preferably is a fragrance, will be emitted to the exterior of the dispenser pump 10 through lower peripheral wall apertures 42 and through the gap 34 between the inner portion peripheral sidewall 28 and the upper portion peripheral sidewall 29. Also some second product will be dispensed through apertures 44 in the bottom portion peripheral wall 29 and apertures 47 in the upper portion peripheral wall 28. This view shows the lower portion peripheral wall apertures 42/44 and the lower portion bottom wall 25 apertures 40/41. The apertures 42/44/47 exit directly to the exterior of the dispensing pump 10 and the latter apertures 40/41 to the lower portion internal area 32. From lower portion internal area 32 the second product will vent through space 34 and apertures 44. The threads 17 on the lower portion inner wall 23 attach the dispensing pump 10 to the neck of container 12 through mating threads 27 on the exterior surface of the neck of the container 12.

Figure 5:
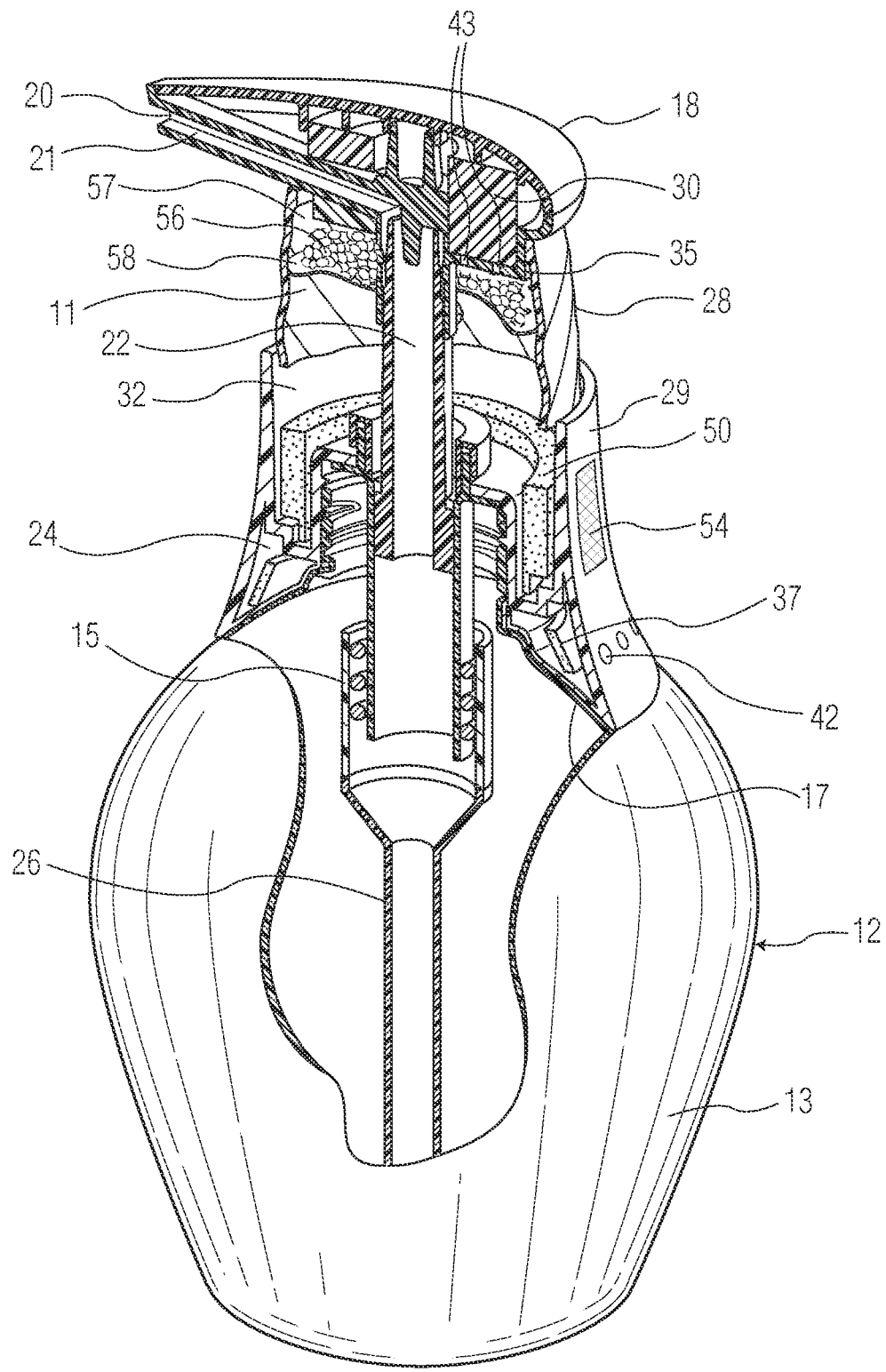
FIG. 5 is a modified embodiment of the pump head of FIG. 1 with apertures in the upper portion peripheral sidewall and lower portion peripheral sidewall, bead units in the lower portion auxiliary area and a compressible fragrance unit in the lower portion internal area.

FIG. 5 is an alternate embodiment of the assembly of the container 12 and the dispensing pump 10. In this embodiment the container 12 is the same as in the other embodiments. The primary modifications from the prior Figures is that a compressible fragrance retainer 50 is located in the lower portion internal area 32 and there is a plate 58 with apertures located in the upper portion internal area 11. This plate 58 will serve to compress the compressible second product retainer 50. This second product retainer can be an organic compressible foam with the second product in the cell structure of the foam. The fragrance beads 56 in the space 57 above the plate 58 will increase the fragrance content of the dispensing pump 10. Upon the actuation of the dispensing pump 10. by depressing top actuator surface 18, the fragrance will be expelled from the dispensing pump 10 through the gap 34 between the upper peripheral wall 28 and the lower peripheral wall 29 and through one of a plurality of vents 54 in lower peripheral wall 29. These vents are larger than the apertures 42 which vent auxiliary area 24. There can be a fragrance band 37 in the auxiliary 24 defined by lower portion peripheral wall 29, lower portion auxiliary wall 17 and lower portion bottom wall 25. The beads 56 above the apertured plate 58 and the second product 30 will vent to the exterior primarily through vents 54 in lower portion peripheral wall 29 and will provide a continual flow of fragrance into a room. Upon the actuation of the dispensing pump, there will be an added burst of fragrance to a room through space 34 between peripheral walls 28 and 29. Fragrance can be continuously emitted through apertures 42 from auxiliary area 24.

Figure 6:
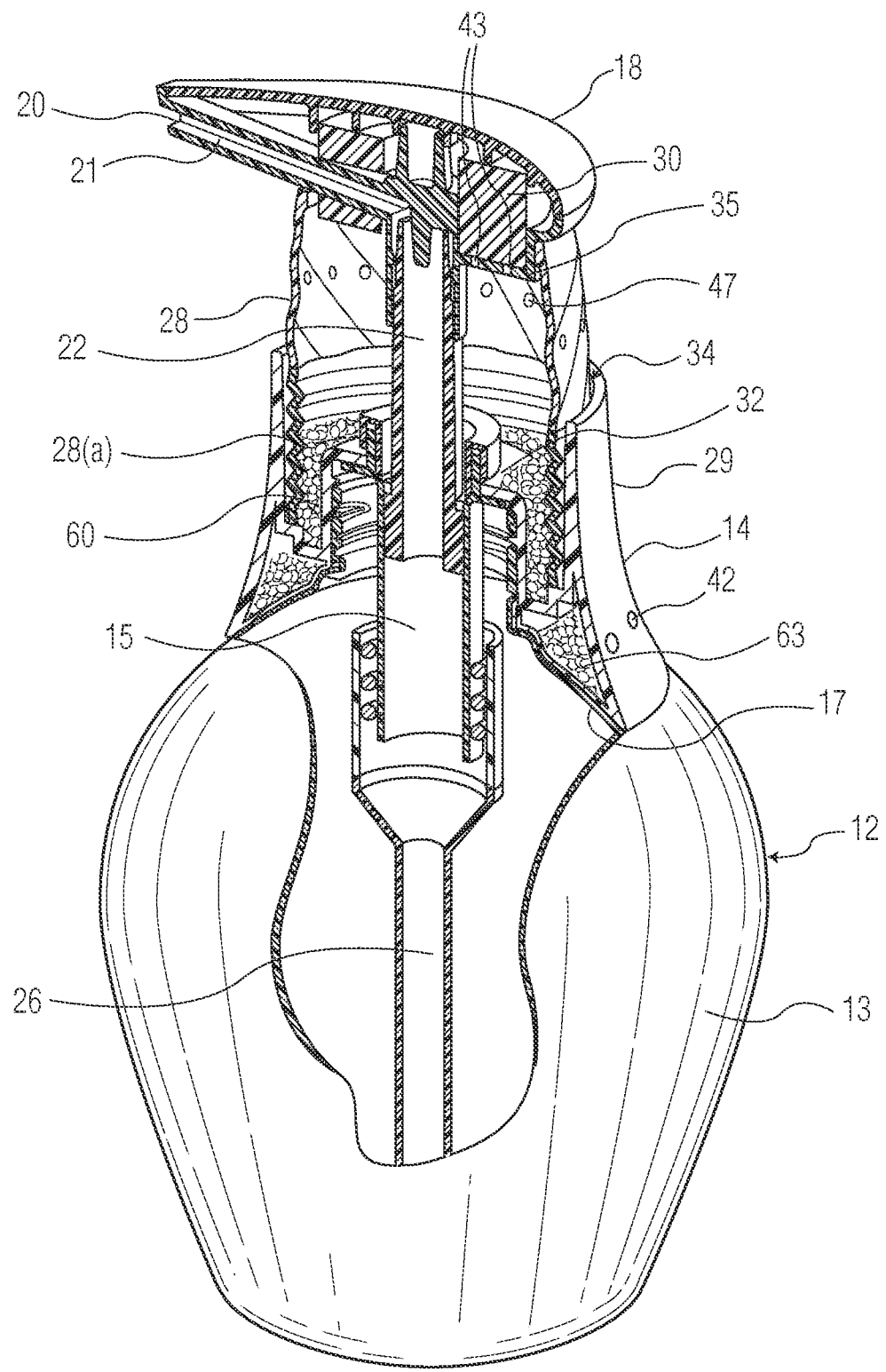
FIG. 6 is an alternate embodiment to the pump head of FIG. 5 with bead fragrance units in the lower portion internal area and a solid fragrance unit in the upper portion internal area along with apertures in the upper portion peripheral sidewall and the lower portion peripheral sidewall.

FIG. 6 discloses a further embodiment of the container and dispensing pump 10 of FIG. 4. In this embodiment there are fragrance beads 63 in the lower portion auxiliary area 24 with the upper portion peripheral side wall 28 having a lower part 28(a) that is collapsible in a folded arrangement. It folds onto itself. This allows for fragrance containing beads 60 to be in the lower portion internal area 32. In this way the beads will not interfere with pushing top actuator 18 downward to dispense the first product and the second fragrance product. The lower part of upper portion of peripheral wall 28 does not move downward but rather collapses in an accordion fashion. If it had a decreased length and had to move downward it would conflict with the beads 60 in the lower portion internal area 32. During a dispensing stroke the fragrance from the fragrance unit 30 and the beads 60 will be emitted from the dispensing pump 10 through apertures 47 in upper portion peripheral wall 28 and some from space 34. Fragrance will be continually emitted from the dispensing pump 10 through apertures 42 from the beads 63 in auxiliary area 24. Other structures are possible for a fragrance source in dispensing pumps. However, those structures are within the present concepts.

Figure 7:
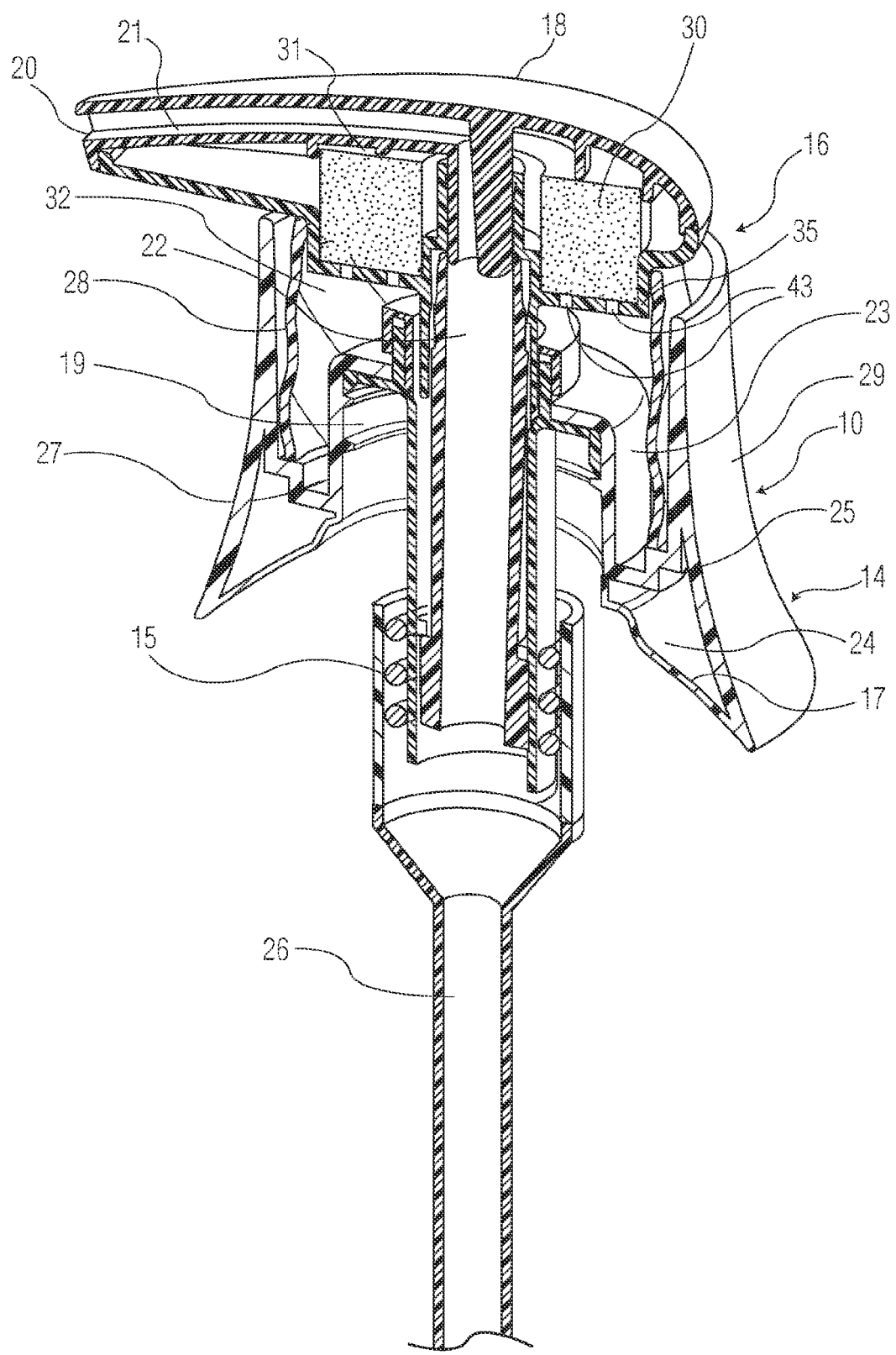
FIG. 7 is an embodiment where the second product is located in the upper portion of the dispenser below the spout channel that delivers the first product to the exterior of the pump.

FIG. 7 discloses an additional embodiment where the second product unit 30, which preferably is a fragrance, is located below the spout channel 21. Otherwise the structure of the upper portion 16 in this FIG. 7 is the same as that in FIGS. 1 and 2. The lower portion 14 is the same as that in FIGS. 1 and 2. The second product unit 30 is supported by support wall 35 which has apertures 43 for the passage of some of the second product into the upper portion internal area 11. This lower wall 35 also can be discontinuous with measured gaps to provide for a calculated dispensing of the second product. Once in this upper portion internal area 11 the second product can be dispensed from the pump head 10 in the same manner as in the pump head of FIGS. 1 and 2. Although the pump head of this FIG. 7 is shown with the second product only in the upper part of upper portion 16, additional second product can be in lower portion 14 as is shown in any of FIGS. 3, 4, 5 and 6. This includes auxiliary area 24. The lower portion 14 of the pump head 10 is the same as in FIGS. 1 and 2 and has been disclosed in detail with reference to those Figures.

The fragrance units can be solid formed units, a gel or polymer beads which contain a fragrance and which are available from International Flavors and Fragrances in Hazlet, N.J. and from Firmenich Incorporated, in Plainsboro, N.J. They also can be in the form of fragrance containing fibers and various forms of gelled fragrances. In addition the fragrances can be adsorbed into various inorganic carriers such as aluminas, silicas and aluminosilicates. They also can be absorbed into the cellular structure of organic foam materials. In any of these forms the fragrances can be incorporated into the pump head structures of the present invention. Further, there are other suppliers of fragrances and fragrance units that can be utilized in the present pump heads.

The pumps and pump bodies are available from pump manufacturers such as Saint Gobain Calmar, Owens-Ill., and AFA Incorporated. The containers can be various blow molded containers of essentially any shape and utilizing various thermoplastics that are conventionally blow molded. These thermoplastics include polyethylenes, polypropylenes, ethylene copolymers, propylene copolymers, polyethylene terephthalate polymers and polyethylene napthalate polymers. The parts usually will be made by injection molding. These are the most useful materials for the construction of the dispensing pump parts with the most useful technique being injection molding.

The invention claimed is:

1. A dispensing pump comprising a pump mechanism, a pump head on one end of the pump mechanism to actuate the pump mechanism, the pump head having an upper portion and a lower portion, the lower portion having an attachment structure for attachment of the pump head to a container, the container adapted to contain a first product, the upper portion having a top wall and a depending peripheral wall, the lower portion having a bottom wall and an upwardly extending peripheral wall, an aperture in the lower portion peripheral wall or an aperture in the upper portion peripheral wall, or a space between the upper portion peripheral wall and the lower portion peripheral wall, wherein the lower portion and the upper portion each has an internal area combining to form an enclosed space for containing a second product, the pump mechanism further comprising a dispensing channel for the first product, the dispensing channel extending through the lower portion at one end and the upper portion at a second end, the upper portion being adapted to pass into the lower portion when the pump mechanism is actuated to force air from the enclosed space, whereby second product can exit the pump head through one of: the aperture in the lower portion peripheral wall, the aperture in the upper portion peripheral wall, and the space between the upper portion peripheral wall and the lower portion peripheral wall.

2. A dispensing pump as in claim 1 wherein the upper portion peripheral wall and the lower portion peripheral wall overlap, the space being a gap between the upper portion peripheral wall and the lower portion peripheral wall.

3. A dispensing pump as in claim 2 wherein there is an auxiliary area in the lower portion for containing a portion of the second product.

4. A dispensing pump as in claim 1 wherein the lower portion peripheral wall or the upper portion peripheral wall has an aperture.

5. A dispensing pump as claim 1 wherein the lower portion peripheral wall has an aperture.

6. A dispensing pump as in claim 1 wherein the upper portion peripheral wall has an aperture.

7. A dispensing pump as in claim 1 wherein the second product is a fragrance emitting substance.

8. A dispensing pump as in claim 1 wherein the the lower portion has an auxiliary area for containing a portion of the second product.

9. A dispensing pump as in claim 1 wherein both the upper portion and the lower portion contain the second product.

10. A dispensing pump as in claim 9 wherein the lower portion has an auxiliary area in the lower portion for containing a portion of the second product.

11. A dispensing pump as in claim 1 wherein the upper portion has a spout to the exterior, a spout channel connecting to the spout, at least a portion of the second product located below the spout channel.

12. A container with a dispensing pump comprising a container with a dispensing pump attached thereto, a pump head on one end of a pump mechanism, the pump head comprising an upper portion and a lower portion, the lower portion having an attachment structure for attachment to the container, the container adapted to contain a first product, the upper portion having a top wall and a depending upper portion peripheral wall, the lower portion having a bottom wall and a lower portion upwardly extending peripheral wall, an aperture in the lower portion peripheral wall or an aperture in the upper portion peripheral wall, or a space between the upper portion peripheral wall and the lower portion peripheral wall, wherein the lower portion and the upper portion each has an internal area combining to form an enclosed space for containing a second product, the pump mechanism further comprising a dispensing channel for the first product, the dispensing channel extending through the lower portion at one end and the upper portion at a second end, the upper portion being adapted to pass into the lower portion when the pump mechanism is actuated to force air from the enclosed space, whereby second product can exit the pump head through one of: the aperture in the lower portion peripheral wall, the aperture in the upper portion peripheral wall, and the space between the upper portion peripheral wall and the lower portion peripheral wall.

13. A container as in claim 12 wherein the container contains a first product and the second product is a fragrance emitting substance.

* * * * *